United States Patent [19]

Boberg et al.

[11] Patent Number: 5,752,946
[45] Date of Patent: May 19, 1998

[54] DISPOSABLE LIQUID ABSORBENT ARTICLE

[75] Inventors: Fredrik Boberg, Alingsås; Carina Hedlund, Kungsbacka, both of Sweden

[73] Assignee: SCA Mölnlycke AB, Göteborg, Sweden

[21] Appl. No.: 737,481
[22] PCT Filed: May 15, 1995
[86] PCT No.: PCT/SE95/00538
 § 371 Date: Jan. 22, 1997
 § 102(e) Date: Jan. 22, 1997
[87] PCT Pub. No.: WO95/31162
 PCT Pub. Date: Nov. 23, 1995

[30] Foreign Application Priority Data

May 16, 1994 [SE] Sweden ................... 9401680

[51] Int. Cl.$^6$ ................................ A61F 13/15
[52] U.S. Cl. .............. 604/385.2; 604/373; 604/387; 604/385.1
[58] Field of Search .................. 604/373, 385.1, 604/385.2, 387, 393, 396

[56] References Cited

U.S. PATENT DOCUMENTS 4,323,070  4/1982  Ternström et al.
5,308,346  5/1994  Sneller et al. ............... 604/385.2

FOREIGN PATENT DOCUMENTS 0 475 419 A1  3/1992  European Pat. Off.
2 156 681  10/1985  United Kingdom.
2 168 253  6/1986  United Kingdom.
WO 88/04547  6/1988  WIPO.

*Primary Examiner*—Robert A. Clarke
*Attorney, Agent, or Firm*—Burns, Doane, Swecker & Mathis, L.L.P.

[57] ABSTRACT

A disposable liquid-absorbing article, such as a diaper (10), sanitary towel or similar, having a substantially longitudinal shape and including an absorption body (12) and a cover (11) enclosing the absorption body with a liquid-pervious inner sheet (17) and an outer sheet (18) and contracting elastics members (23) in contact with at least one of the sheets to give the article its shape in an in-use position. The cover sheet on which the elastics members are applied, is connected to the inside and outside of the absorption body respectively, and the elastics members (23) extend with at least one substantially continually curved portion (24, 25) over at least an area of the absorption body. The strive of the elastics members to contract and the contact of the elastics members with one of the sheets, exert a tension force on the sheet in a direction towards the curvature center of the elastics members, whereby this force is transferred and absorbed by the absorption body.

14 Claims, 4 Drawing Sheets

DISPOSABLE LIQUID ABSORBENT ARTICLE

The present application claims the benefit of International Application No. PCT/SE95/00538, which was filed on May 15, 1995, and which claims the priority of Swedish Patent Application No. 9401680-5, which was filed on May 16, 1994.

TECHNICAL FIELD OF THE INVENTION

The present invention relates to a disposable liquid-absorbent article according to the preamble of the appended claim 1.

DESCRIPTION OF RELATED ART

Liquid-absorbent articles, for example diapers, provided with elastics in order to give the article its shape in an in-use position, are known in the prior art. In most articles of this kind the main purpose of the elastics is to provide, at the wearer's crotch, a raised edge, sealing against the wearer's legs. Hitherto known solutions, however, offer a limited capacity concerning the ability to locally collect and contain larger volumes of for instance faeces and urine.

From for example U.S. Pat. No. 3,860,003, a diaper is known, where leg elastics provide a circumferential cuff around the legs. In the spread-out position of the article, the elastics are fully rectilinear and substantially extending along the side of the absorption body in order to make the edge of the diaper seal against the legs in an in-use position.

U.S. Pat. No. 4,050,462 refers to a diaper with elastics extending rectilinearly in the flat condition of the diaper and serves to contract the crotch section of the diaper and, by folding, increase the surface and the volume per length unit for the absorption body in order to achieve an enhanced absorption effect.

WO 88/00010 shows a diaper having substantially rectilinear elastics, forming a V-shaped configuration. The elastics extend over the absorption body of the diaper and delimit an area that is altered in shape by the contracting effect of the elastics. By the extension of the elastics with rectilinear sections, a folding of the article as a whole is substantially achieved as a result of the tendency of the elastics to reduce the entire length of the article.

U.S. Pat. No. 4,801,345 shows a method for the manufacture of diapers. The method includes the application of elastics along the crotch section of the diapers. The elastics hereby extend concavely outwards along the longitudinal edges of the diaper and completely to the side of the absorption body. The purpose of the elastics is mainly to achieve a sealing contact between the edge of the diaper and the wearer's legs. A further effect will be a certain contraction and folding of the absorption body over the crotch section.

EP 0 219 326 shows a diaper with elastics, extending completely rectilinearly in the diaper's flat state and completely to the side of the absorption body. Elastics are arranged partly at the outer edge of the diaper on each side of the crotch section and partly in an edge-band on each side of the absorption body. In addition to maintaining an upstanding, sealing edge by way of the edge-band, the elastics ensure a certain folding and contraction of the absorption body.

GB 2 234 157 relates to a diaper with elastics extending around the waistline of the trousers, and along the edge of the crotch section against the wearer's legs and also across the crotch section. The elastics for sealing around the legs reduce the risk of leakage, while the elastics across the crotch section are merely arranged to enable a rational application of continuous elastic cord. The composition and method is specially adapted to trouser-shaped diapers.

SUMMARY OF THE INVENTION

The object of the present invention is to provide a liquid-absorbent article for disposable use, which in a user position is given a highly efficient collecting shape.

Ever since diapers with leg elastics according to U.S. Pat. No. 3,860,003 became common during the seventies a great number of patent applications referring to diaper elastics have been filed worldwide.

Elastics have been applied along and/or across the diaper in order to create a 3-dimensional shape or leakage barriers.

Elastics have further been applied in a curved shaped along the edge areas of the cover-sheet outside of the side-edges of the absorption body, whose curved shape was chosen for better adaptation to the user's body shape.

By the present invention an entirely new elastic effect has been created, yielding immense product advantages.

BRIEF DESCRIPTION OF THE DRAWINGS

The invention will in the following be described in greater detail by way of two embodiments with reference to the appended drawings, in which.

DETAILED DESCRIPTION OF PREFERRED EMBODIMENTS

As an embodiment, an article for collection of liquid and faeces, particularly representative for the invention, has been chosen, namely a diaper for so called heavy incontinence, i.e. not infants but grown-up persons, who as a result of disease or old age suffer from severe incontinence troubles.

Figure 1:
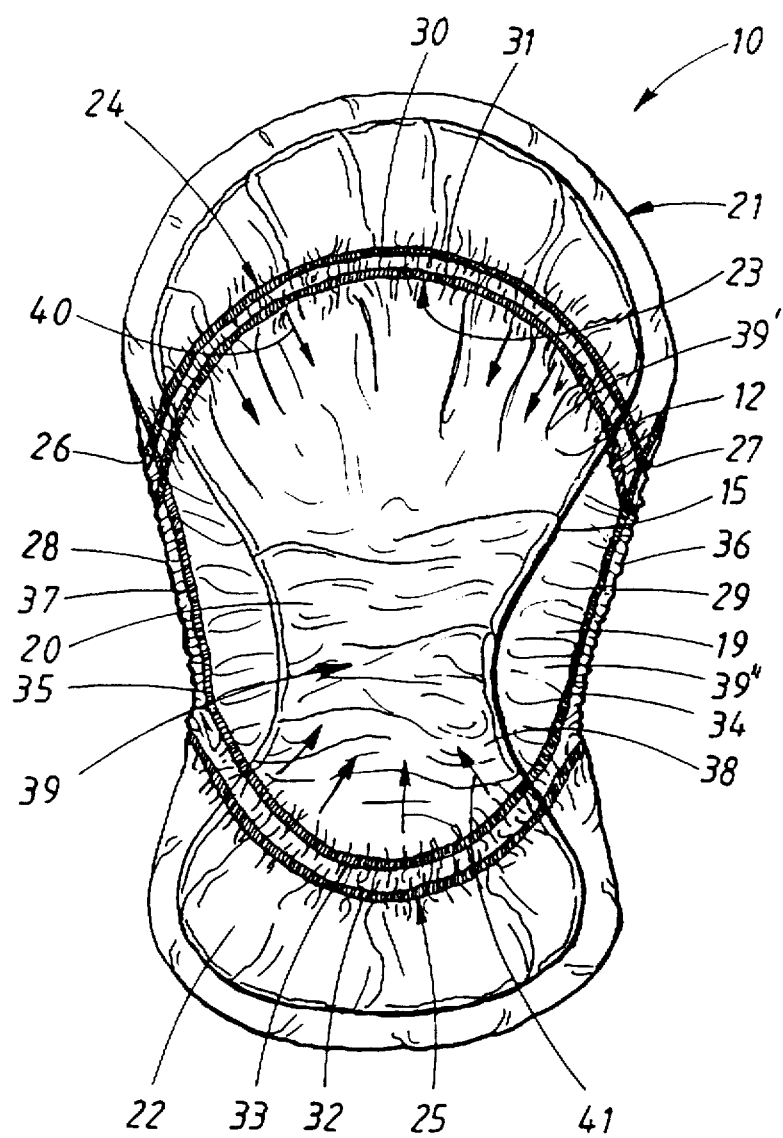
FIG. 1 shows a plane elevation of an article according to the invention according to a first embodiment in the shape of a diaper.
Figure 2:
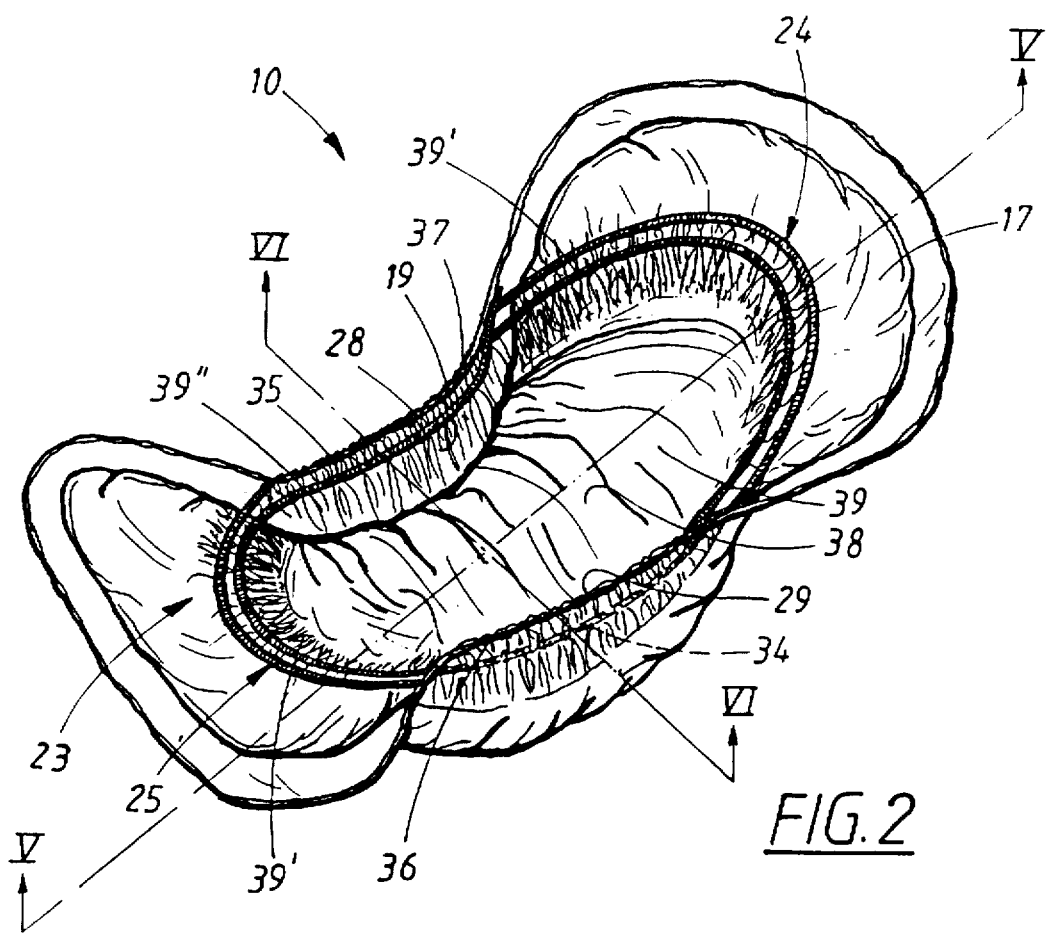
FIG. 2 is a perspective view of the diaper according to FIG. 1 substantially shaped into an in use position.
Figure 4:
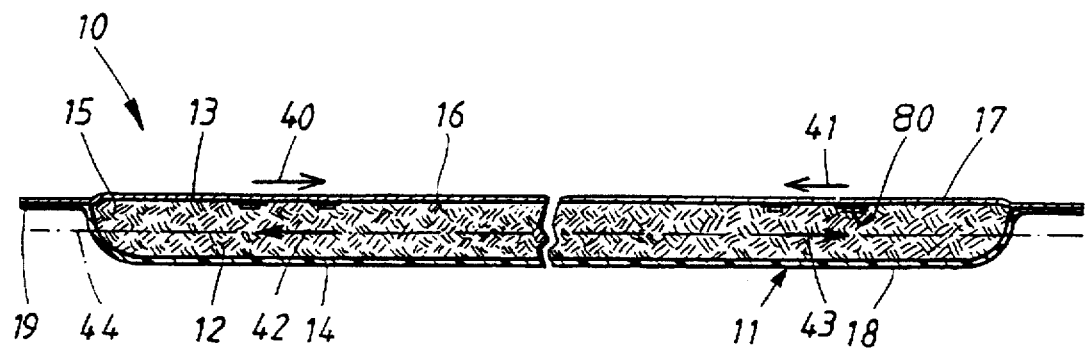
FIG. 4 is a longitudinal cross-section through the diaper in a plane, extended condition along the line V—V in FIG. 2.

As is apparent from the first embodiment, best shown in FIG. 1, 2 and 4, the diaper consists of a cover 11, enclosing a core in the shape of a absorption body 12. In a flat, spread-out condition, shown in FIG. 4, the core displays a relatively flat main shape with two main surfaces facing away from each other, namely an inside 13 intended to face the user, and an outside 14, intended to be facing outwards. The absorption body 12 further displays a circumferential, rounded edge-portion 15, giving the absorption body 12 an expedient outer contour anatomically adapted to the wearer's body. Even if the absorption body 12 is mainly of equal thickness overall, it is in practice advantageously provided with a central portion 16 having a somewhat greater thickness (not shown).

The cover 11 in the shown embodiment is formed by two sheets 17, 18 with mutually different characteristics, which sheets 17, 18 are applied towards the inside 13 and the outside 14 respectively of the absorption body 12 and seal off the absorptions body by both sheets being joined together outside of the edge-portion 15 of the absorption body, and form a circumferential flange-like edge-portion 19 for the diaper as a whole. Both the sheets 17, 18 are placed in contact with each other at the edge-portion 19 and are mutually joined with adhesives.

The special components used to form the shown diaper may be any components commonly used for such purposes. The sheet 17, which is applied on the inside 13 may be of any soft, flexible, liquid-pervious material, such as fibre cloth (non-woven) or a soft perforated plastic film of polyethylene or similar. The sheet 18 on the outside 14 is of a liquid-impermeable material, such as a thin (for example 20µ) plastic film of polyethylene, polypropylene, polyvinylcloride or similar. The absorption body may consist of cellulosic fibres, tissue laid out by compressed air, different types of superabsorbent material etc.

As is best shown in FIG. 1, the diaper in the shown embodiment has the main shape of an asymmetric hourglass or a peanut-shell displaying a waist or a crotch area 20, which in one direction is expanded towards a back portion 21 and a frontal portion 22, which portions are intended to contact corresponding portions of the wearer in an in use position. The absorption body 12 tapers off to a greater extent than the outer contour of the diaper 10 which yields a greater breadth of the diaper's edge-portion 19 in level with the crotch area 20.

In order to shape the diaper 10 into its expedient shape in an in-use position, the diaper is provided with contracting elastics 23, arranged in a configuration and position unique to the invention. An expedient shape is a shape, which enables the diaper in an in-use position to contain large amount of liquid of solid body exudate, by absorption and by a shape-wise containment of the products, be they urine, blood or other body liquids or faeces. To this end the elastics 23 are at least partly provided with ark-shaped curved portions 24, 25, extending over the absorption body 12. In the shown embodiment, two ark-shaped continually curved elastic portions 24, 25 are provided, which via edge-elastics (see below) essentially meet at their ends at two crossings 26, 27 near the longitudinal edge-portions 28, 29 of the diaper.

The elastics 23 are joined to at least one of the sheets 17, 18 in the cover 11 and is joined to the liquid pervious sheet 17 in the first embodiment. In the shown embodiment, the elastics are applied on the inside of the sheet 17, i.e. between the absorption body and the sheet, but may of course be applied to the outside of the sheet as an alternative. The elastics consist of longitudinal elastic members, having, for example, a cord- or band-shaped core of a highly elastic material, for example rubber and a wrapped-around thread cover that can be bonded with adhesives and enable anchorage of the elastic core in the sheet 17 of the diaper, at the same time as the elastic core allows elastic displacements.

The elastics strives to contract and the elastic cords or bands are to this end prestressed, i.e. stressed to a certain extent before anchoring to the sheet 17 of the diaper. The anchoring is achieved with adhesive 80 applied in certain areas of the length of the elastics or along its entire length. In the shown embodiment, each of the ark-shaped curved portions 24, 25 are arranged with double elastics, i.e. two along each other extending elastic members 30, 31, 32, 33, of which one of the elastic members 33 in one of the curved portions 25 turns into edge-elastics 34, 35, i.e. extending along a section of the two longitudinal edges 28, 29 of the diaper up to the crossing 26, 27 with the elastic members, 30, 31 in the opposite curved portion 34. In the shown embodiment the edge-elastics 34, 35 substantially extend linearly, but they may as well have an arc-shaped, but weak curvature, i.e. a large curvature radius.

In FIG. 1, the diaper is essentially shown in a plane elevation, i.e. spread-out, but in such a condition that the contracting effect of the elastics is visible.

FIG. 2 shows the diaper shaped into an in-use condition. This shape is formed as soon as one starts to handle the diaper, which effect is described in greater detail below. As long as the diaper is flat, essentially no shaping takes place, apart from that the absorbtion body is somewhat compressed. The desired shape may be forcibly initiated when bending the diaper whilst pressing down the area 38 within the elastics by hand before the diaper is brought to its in-use position. By the tendency of the curved elastics to contract and by its anchorage in the sheet 17 of the cover, along with the bond between the sheet and the absorption core, the elastics in conjunction with the deformation characteristics of the cover and the absorption body 12 have formed substantially perpendicular pool walls 39' relative to the flat inside of the article. The cover-portions outside the side edges of the absorption body in the crotch area of the article form the pool walls 39", which together with the pool walls 39' enclose a pool-like space.

Figure 3:
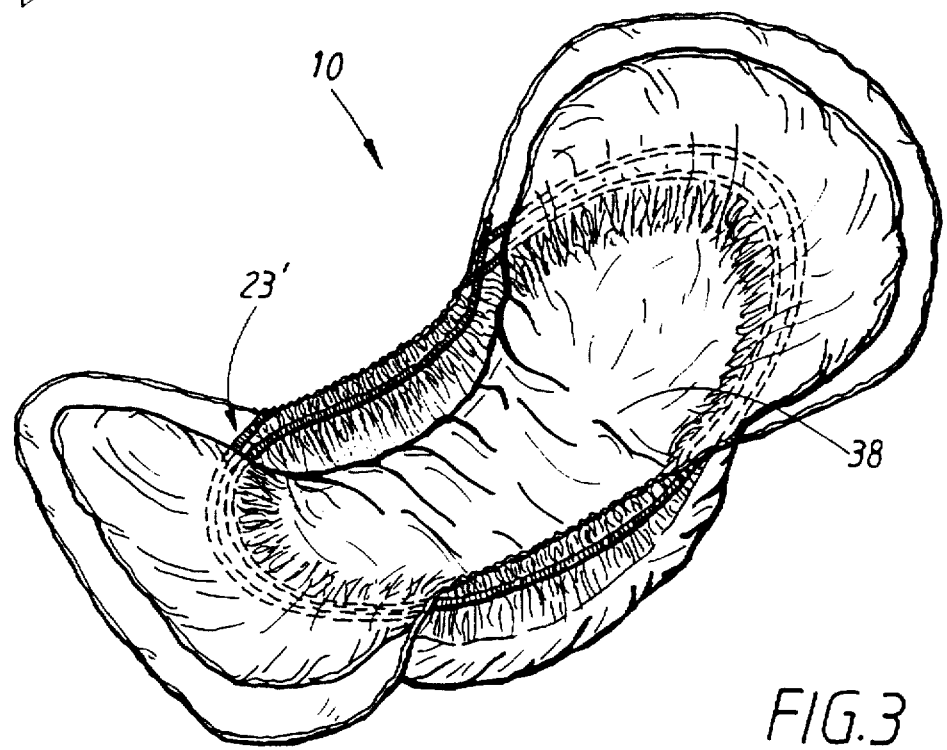
FIG. 3 is a perspective view of the article according to the invention in a second embodiment shaped into an in-use position.

In FIG. 3 a view corresponding to FIG. 2 is shown of a second embodiment of the diaper where the elastics, here referred to as 23', have the same configuration as in the first embodiment, but is bonded to the outer sheet 18 of the cover, i.e. the liquid-impermeable sheet. Even in this case, the elastic cords or bands may advantageously be applied by way of adhesive to the inside of the sheet 18. This must in turn be bonded to the absorption body across its inside. A corresponding, expedient pool is essentially achieved also in this embodiment. Here it is extra important that the forces applied on the diaper by the curved portions of the elastics are helped by outer forces, before these elastic portions cause the required deformation of the diaper in order to form the vertical pool walls.

Both embodiments, the broader section of the edge-portion 19 situated just in front of the crotch area 20, is raised by the tendency of the elastics to contract, i.e. reduce its length. The raised longitudinal edges 36, 37 strive to contact the wearer's body in an in-use position, in practice on the inside of the thighs, in order to thereby form a highly liquid-pervious seal against the body. Especially in the first embodiment according to FIG. 2, marked substantially vertical pool walls are formed on the inside of the curved elastic portions. Additionally, a certain folding arises as a result of the elastics contraction of the sheet in a sideways direction as well. The curved pool walls may as mentioned above be substantially perpendicular relative to the line along the essentially flat bottom of the pool. The curved pool walls may, through choosing the pre-stressing of the elastics and the deformation tendency of the absorption body, form an acute or blunt angle to said line along the pool bottom. When the angle is acute, the pocket-like space is obtained closest to the elastics. The circumferential elastics 23 thus form an upper edge of the pool 39, serving as a containment area for body products, which is particularly valuable in more severe cases of incontinence where the volumes may become relatively large. Faeces may be contained in this space without the risk of it passing beyond the containment area of the diaper. The absorption body 12, particularly the part within the elastics 23, serves the purpose of absorbing liquid, while the pool walls also serves the purpose of preventing leakage of liquid outside the diaper, before the absorption body 12 has had time to completely absorb the entire liquid volume. The raised edge-portions 19 also contains liquid, which has not been immediately absorbed by the absorption body 12 because of the precision of the diaper, for example when the wearer is in a position laying sideways. As soon as the wearer alters body position the liquid can thereby be absorbed by the absorption body.

Figure 5:
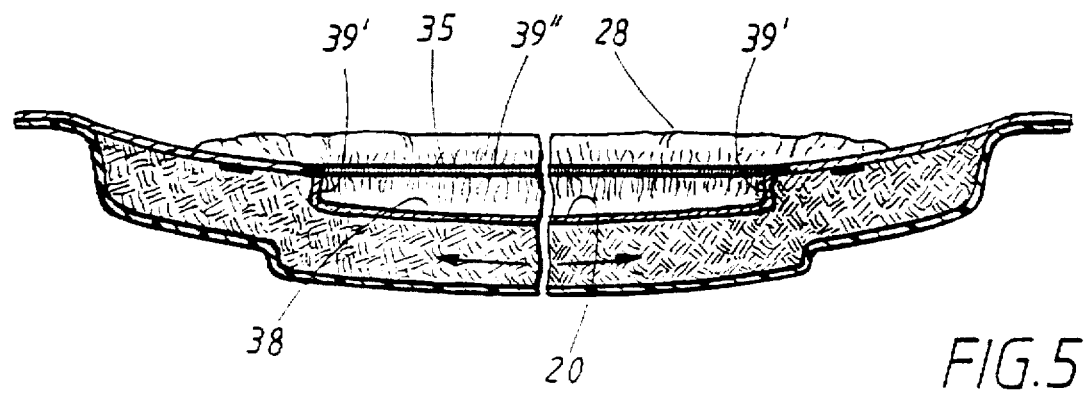
FIG. 5 is a corresponding longitudinal cross-section through the diaper, shaped into an in-use position, along the line V—V in FIG. 2, whilst
Figure 6:
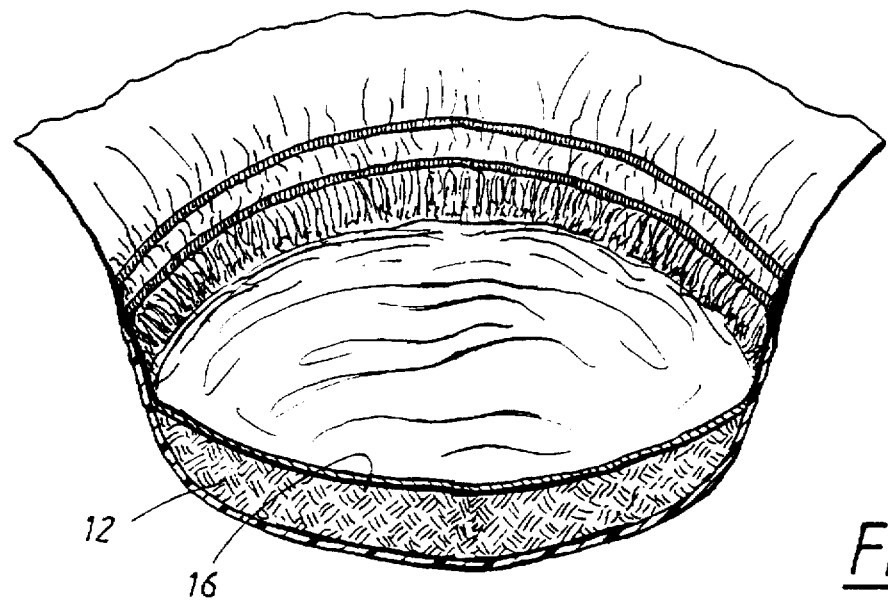
FIG. 6 is a cross-section through the diaper shaped into a user position along the line VI—VI in FIG. 2 and FIG. 7 diagrammatically shows an additional embodiment of the diaper.

The longitudinal section in FIG. 4 and 5 and the cross-section in FIG. 6 illustrates the shaping effect of the elastics, which will be described in greater detail. The shaping effect of the elastics is achieved by the elastics being contracting and thus striving to reduce their lengths. By the anchorage of the elastics in the cover, the cover is brought along in the contracting movement of the elastics. The cover sheets are in turn bonded to the absorption body across their surfaces, whereby tension forces in the plane of the cover sheets are transferred to the absorption body. Since the elastics over the main part of their extension of the absorption body has been applied in a curved shape, the contracting effect results in that the elastics in each point over the curved portion applies a force component 40, 41, see FIG. 1 and 4, directed towards the current curvature centre for each point on the curved portion. If the curved portions have varying curvature radii, different curvature centres exist for each and every point. The absorption body 12 of the diaper, however, has a certain resistance against compression, which is illustrated in FIG. 4 with reaction force components 42, 43, which thus counteracts the contraction forces 40, 41 of the elastics. In a preferred embodiment the resistance against compression is greater than the deformation resistance across the symmetry plane 44 of the slab-shaped absorption body, i.e. in a direction across the direction of the forces 42, 43 in the plane of the paper. The absorption body 12 preferably consists of a so called fluff-mass of cellulose and is relatively easily bent together with the cover 11, but still displays a certain compression resistance. The characteristics result in that the torque moments are caused by the action-reaction forces 41, 43 and 40, 42 respectively creates a deformation of the article in areas with ark-shaped elastics, which deformation is symbolized by the circular ark-lines 41, 49, 50–51 which diagrammatically represents the local direction of bending. By the positioning of the elastics outside the symmetry plane 44, a bending moment of the absorption body 12 arises already in the plane condition. The article, however, has such a degree of stiffness that it does not deform in a plane condition whereby this deformation is first initiated when handling the article.

FIG. 5 illustrates the pool formed by the elastics, which is delimited by the substantially perpendicular pool-walls 39' along the ark-shaped elastics and the pool-walls 39" formed by portions of the cover extending outside of the absorption body. These portions are raised by the action of the edge elastics 34, 35 in combination with the ark-shaped elastics.

The cross-section according to FIG. 6 shows that the pool is relatively deep and whereby it may contain large amounts of exudations.

I the embodiments shown i FIG. 1–6 the elastics as whole forms a closed loop in each completed diaper.

Figure 7:
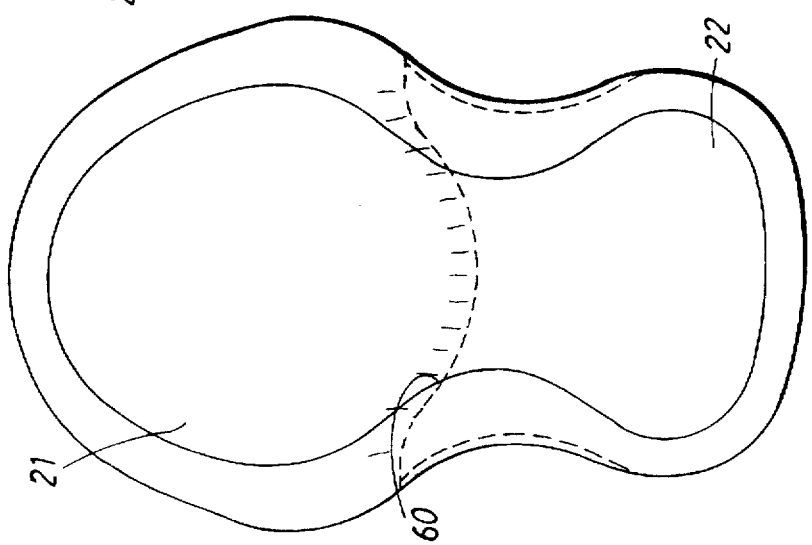

FIG. 7 diagrammatically shows an embodiment of the diaper where the elastics extend across the crotch area 20 with a curved elastics portion 60, forming the delimiting transverse wall 61. In this case a division between the back-portion 21 and the front-portion 22 of the diaper, whereby faeces and urine and an increase volume ??? for the containment space for faeces.

Figure 8:
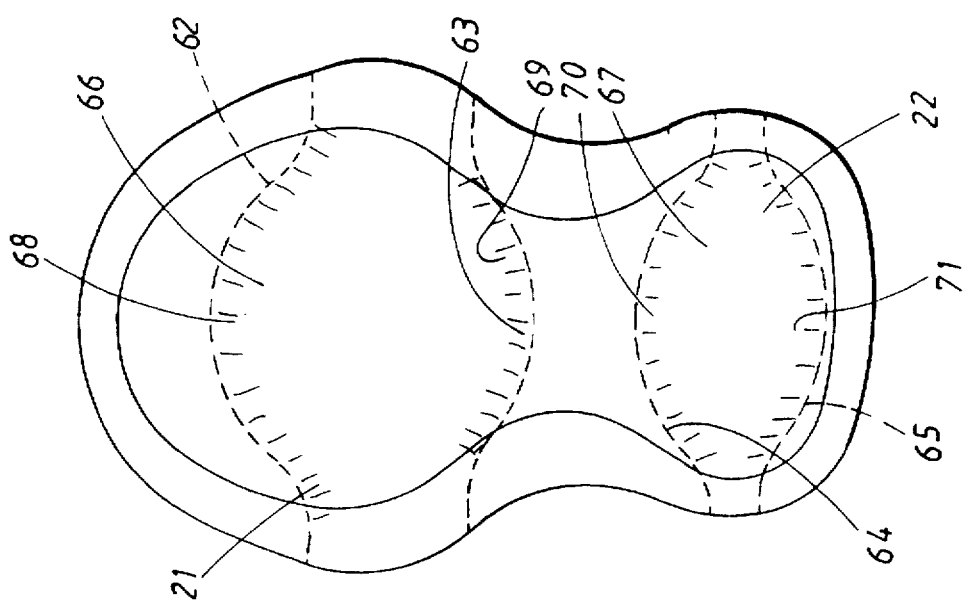
FIG. 8 diagrammatically shows a further embodiment of the diaper.

FIG. 8 shows yet another embodiment, where the back-portion 21 and the front-portion 22 each have a pool-like space 66, 67 formed by two curved elastics portions 62, 63, 64, 65, with transversal pool-edges 68–71 inside each curved portion.

Figure 9:
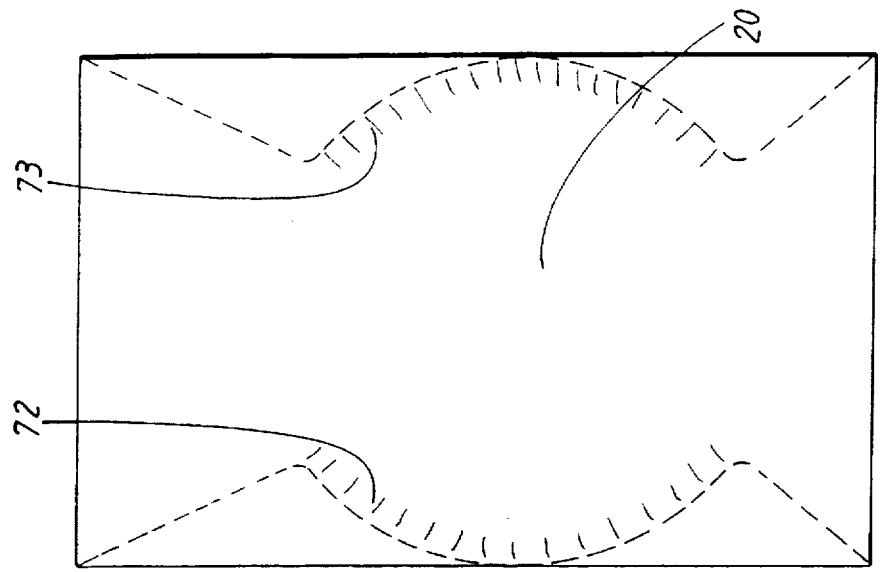
FIG. 9 diagrammatically shows a further embodiment of the diaper.

FIG. 9 shows an alternative embodiment, in which the main shape of the diaper in a flat condition may be substantially rectangular. An our-glass shape with a tapering crotch portion 20 is obtained by the contracting action of the elastics. Even here transversal pool-edges 72, 73 are formed, providing an effecting barrier against edge leakage.

The invention is not limited to the embodiment described above and illustrated in the drawings, but may be varied within the scope of the appended claims. For example, the closed elastics loop may be replaced by separate curved elastics portions. These may for example by arranged with a different positioning, for example across the crotch portion 20 in order to separate faeces and urine from each other. Other articles that diapers for heavy incontinence may be applicable, such as baby diapers, sanitary towels, or similar. The term "a substantially continually curved portion" primarily denotes a arc-shaped or curve-shaped curved portion, but may also include a combination of several rectilinear portions, preferably at least three rectilinear portions as a replacement for a semi-circular ark or similar.

We claim:

1. A disposable liquid-absorbing article, such as a diaper or sanitary towel having a substantially longitudinal shape comprising;

- an absorption body with an inside facing inwardly and an outwardly facing outside,
- a cover enclosing the absorption body with a liquid-pervious inner sheet against the inside of the absorption body and an outer sheet against the outside of the absorption body, and
- contracting elastics members in contact with at least one of the sheets to bring the article its shape in an in-use position,
- the cover sheet on which the elastics members are applied, is connected to at least one of the outside and the inside of the absorption body,
- said elastics members extend with at least one substantially continually curved portion over at least an area of the absorption body,
- said elastic members, by striving to contract and by their contact with one of said sheets exerts a tension force on said one sheet in a direction towards a centre of the curved portion, whereby this force is transferred and absorbed by the absorption body,
- the absorption body is made of a material which makes it easily bent but at the same time at least to a high extent resistant to compression by tension forces against the curved portion of the curved elastics members,
- the elastics members are applied with such a pre-stressing that said tension forces caused by the pre-stressing and the curvature radius deforms the article for the formation of a, in relation to the plane of the article, pool edge along the curved elastics, when bending of the article is initiated by the user.

2. The article according to claim 1, wherein said elastics members extend along the curved portion from one to another of the longitudinal edge-portions.

3. The article according to claim 1, wherein said elastics members form a closed circumference enclosing a pool-like space formed by the elastics.

4. The article according to claim 3, wherein the closed circumference is formed by two curved portions that merges into edge-elastics extending along the longitudinal edge-portions of the article at a crotch area.

5. The article according to claim 4, wherein the absorption body tappers off at the crotch area and the cover at the crotch area and at said longitudinal edge-portions forms a raised portion which is raised into an in-use position and is included in said pool.

6. The article according to claim 1, wherein the absorption body is made of a fluff-mass of cellulose, optionally with embedded particles of fibres of a super-absorbent material.

7. The article according to claim 1, wherein the absorption material is made of synthetic fibres and super-absorbent material.

8. The article according to claim 1, wherein the absorption material is made of a foam.

9. The articles according to claim 1, wherein the article has a frontal portion, a backportion and a crotch area, the curved elastics portions are applied for the formation of a first enclosed area displaced towards the frontal portion and intended for the containment of urine and for the formation of a second closed area displaced towards the backportion and intended for containment of faeces.

10. The article according to claim 1, wherein the article has a transversal curved elastics member for the formation of a, relative to the plane of the article, raised barrier wall.

11. The article according to claim 1, wherein the elastics members extend with one substantially continually curved portion with respect to the sheet to which it is attached.

12. The article according to claim 11, wherein the elastic members are attached at longitudinal end portions of the article.

13. The article according to claim 12, wherein the elastics members extend from one longitudinal edge to another longitudinal edge.

14. The article according to claim 11, wherein the elastic members are attached at longitudinal end portions of the article.

* * * * *